United States Patent [19]

Conway et al.

[11] Patent Number: 4,704,157

[45] Date of Patent: Nov. 3, 1987

[54] HERBICIDAL 5-(3-SUBSTITUTED-ISOXAZOYL OR ISOTHIAZOYL)-CYCLOHEXANE-1,3-DIONE DERIVATIVES

[75] Inventors: Richard J. Conway, Essendon; Keith G. Watson, Box Hill North; Graeme J. Farquharson, Reservoir, all of Australia

[73] Assignee: CI Australia Ltd., Melbourne, Australia

[21] Appl. No.: 860,796

[22] Filed: May 8, 1986

Related U.S. Application Data

[62] Division of Ser. No. 604,967, Apr. 27, 1984, Pat. No. 4,604,132.

[30] Foreign Application Priority Data

May 6, 1983 [AU] Australia ............................. PF9198

[51] Int. Cl.$^4$ ................... A01N 43/80; C07D 275/02; C07D 261/08
[52] U.S. Cl. ........................................ 71/90; 548/193; 548/213; 548/214; 548/247; 548/200; 548/136
[58] Field of Search ............... 548/184, 213, 233, 244; 71/88, 90, 106

[56] References Cited

U.S. PATENT DOCUMENTS 3,950,420  4/1976  Sawaki et al. ........................ 71/88
4,033,754  7/1977  Sawaki et al. ........................ 71/106

FOREIGN PATENT DOCUMENTS 66195    5/1982  European Pat. Off. ............ 546/334
3230087  2/1984  Fed. Rep. of Germany ......... 71/90

Primary Examiner—Donald G. Daus
Assistant Examiner—Brian R. Leslie
Attorney, Agent, or Firm—Cushman, Darby & Cushman

[57] ABSTRACT

The invention concerns novel compounds of the formula I

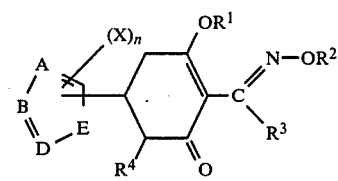

wherein:
A, B and D are selected from CH and N;
E is selected from oxygen and sulfur;
X are selected from halogen, nitro, cyano, alkyl, substituted alkyl, hydroxy, alkoxy, substituted alkoxy, alkenyl, alkenyloxy, alkynyl, alkynyloxy, acyloxy, alkoxycarbonyl, alkylthio, alkylsulfinyl, alkylsulfonyl, sulfamoyl, substituted sulfamoyl, alkanoyloxy, benzyloxy, substituted benzyloxy, phenyl, substituted phenyl, amino, substituted amino, and the groups formyl and alkanoyl and the oxime, imine and Schiff base derivatives thereof;
$R^1$ is selected from hydrogen, alkyl, alkenyl, alkynyl, substituted alkyl, alkylsulfonyl, arylsulfonyl, acyl and an inorglanic or organic cation;
$R^2$ is selected from alkyl substituted alkyl, alkenyl, haloalkenyl, alkynyl and haloalkynyl;
$R^3$ is selected from alkyl, fluoroalkyl, alkenyl, alkynyl, and phenyl;
$R^4$ is selected from hydrogen, halogen, alkyl, cyano and alkoxycarbonyl; and
n is 0 or an integer chosen from 1 and 2.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

7 Claims, No Drawings

HERBICIDAL 5-(3-SUBSTITUTED-ISOXAZOYL OR ISOTHIAZOYL)-CYCLOHEXANE-1,3-DIONE DERIVATIVES

This is a division of application Ser. No. 604,967, filed Apr. 27, 1984 now U.S. Pat. No. 4,604,132.

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For Example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Austrailian Pat. No. 464 655 and its equivalents such as UK Pat. No. 1 461 170 and U.S. Pat. No. 3,950,420.

More recently at the 1980 British Crop Protection Conference ("1980 British Crop Protection Conference—Weeds, Proceedings Vol. 1, Research Reports", pp 39 to 46, British Crop Protection Council, 1980), a new cyclohexane-1,3-dione grass herbicide code named NP 55 (2-N-ethoxybutrimidoyl)-5-(2-ethylthio-propyl)-3-hydroxy-2-cyclohexen-1-one) was announced. This compound is disclosed in Australian Pat. No. 503 917 and its equivalents.

It has now been found that a new group of cyclohexane-1,3-dione derivatives which have a 5-(5-membered heteroaryl ring) substituent exhibit particularly useful herbicidal activity.

Accordingly the invention provides a compound of formula

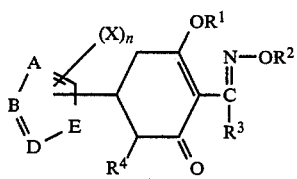

wherein
A, B and D are independently selected from CH and N provided that at least one of A, B and D is selected from N;
E is selected from oxygen and sulfur;
X, which may be the same or different, are independently selected from the group consisting of: halogen; nitro; cyano; $C_1$ to $C_6$ alkyl; $C_1$ to $C_6$ alkyl substituted with a substituent selected from the group consisting of halgen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxyl; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)-sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; phenyl; substituted phenyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ alkyl sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R_3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

$R_4$ is selected from the group consisting of: hydrogen; halogen; cyano; $C_1$ to $C_6$ alkyl; and ($C_1$ to $C_6$ alkoxy)-carbonyl; and n is 0 or an integer chosen from 1 and 2.

When in the compound of formula I X is chosen from the groups formyl and $C_2$ to $C_6$ alkanoyl and the oxime, imine and Schiff base derivatives thereof, the nature of the oxime, imine and Schiff base derivatives is not narrowly critical. Although not intending to be bound by theory, it is believed that in the plant the (substituted) imine group may be removed to give the corresponding compound of formula I in which X is formyl or $C_2$ to $C_6$ alkanoyl. Suitable values for the groups formyl and $C_2$ to $C_6$ alkanoyl and the oxime, imine and Schiff base derivatives thereof include groups of the formula $-C(R^7)=NR^8$ wherein $R^7$ is chosen from hydrogen and $C_1$ to $C_5$ alkyl, and $R^8$ is chosen from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N+$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl groups is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R_1$ is hydrogen the compounds of the invention may exist in any one of four tautomeric forms as shown below wherein $\phi$ represents the group

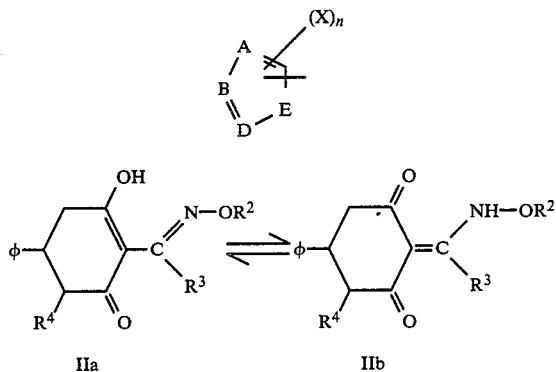

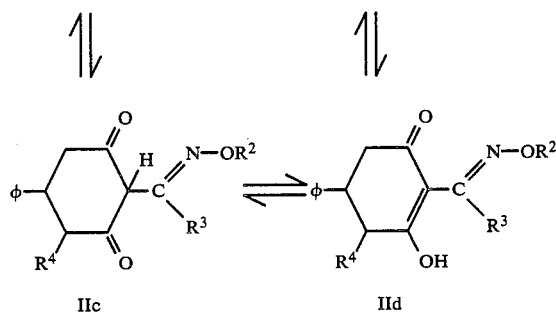

The compounds of the invention include: oxazole and thiazole derivatives of formulae Ia to If

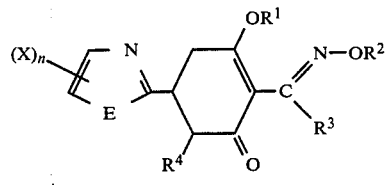

Ia E = O
Ib E = S

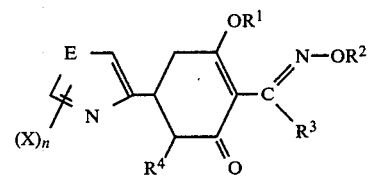

Ic E = O
Id E = S

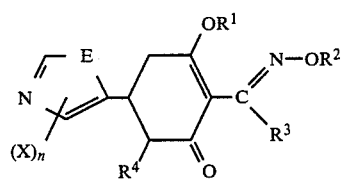

Ie E = O
If E = S;

isoxazole and isothiazole derivatives of formula Ig to Il

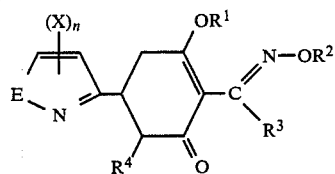

Ig E = O
Ih E = S

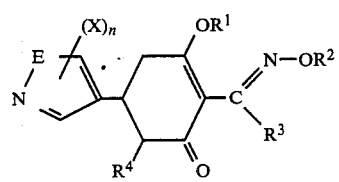

Ii E = O
Ij E = S

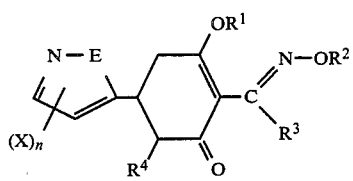

Ik E = O
Il E = S;

1,2,3-oxadiazoles and 1,2,3-thiadiazoles of formula Im to Ip

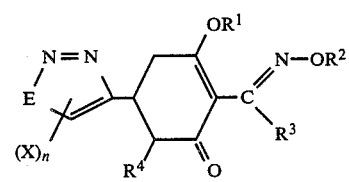

Im E = O
In E = S

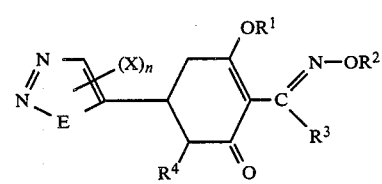

Io E = O
Ip E = S;

1,2,4-oxadiazoles and 1,2,4-thiadiazoles of formula Iq to It;

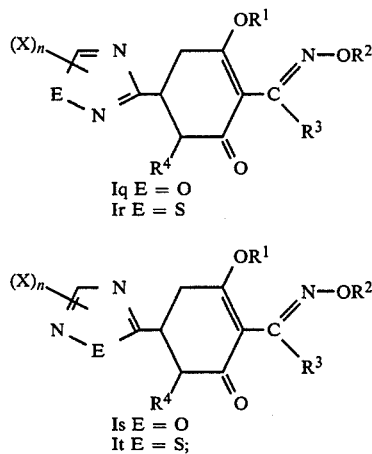

Iq E = O
Ir E = S

Is E = O
It E = S;

1,3,4-oxadiazoles and 1,3,4-thiadiazoles of formula Iu and Iv

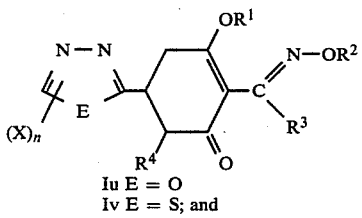

Iu E = O
Iv E = S; and 1,2,3,4-oxadiazoles and 1,2,3,4-thiadiazoles of formulae Iw and Ix

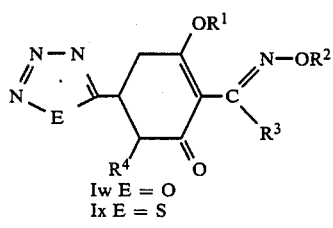

Iw E = O
Ix E = S

Preferred compounds of the invention include those compounds of formula I wherein:
A, B and D are independently selected from CH and N;
E is selected from oxygen and sulfur;
X, which may be the same or different, are independently selected from the group consisting of $C_1$ to $C_6$ alkyl, $C_1$ to $C_6$ alkoxy, $C_1$ to $C_6$ alkylthio, halogen, amino, N-($C_1$ to $C_6$ alkyl)amino, N,N-di($C_1$ to $C_6$ alkyl)amino, $C_2$ to $C_6$ alkanoyl, phenyl, substituted phenyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl, and $C_1$ to $C_6$ alkyl substituted with a substituent selected from the group consisting of halogen, nitro, hydroxy, $C_1$ to $C_6$ alkoxy and $C_1$ to $C_6$ alkylthio;
$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra(alkyl)ammonium ions wherein alkyl is selected from $C_1$ to $C_6$ alkyl and $C_1$ to $C_6$ hydroxyalkyl;
$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_2$ to $C_6$ haloalkynyl;
$R^3$ is selected from $C_1$ to $C_6$ alkyl;
$R^4$ is selected from hydrogen, halogen and ($C_1$ to $C_6$ alkoxy)carbonyl; and
n is zero or an integer selected from 1 and 2.

More preferred compounds of the invention include those compounds of formula I wherein:
A, B and D are selected from CH and N provided that no more than two of A, B and D is selected from N;
E is selected from oxygen and sulfur;
X which may be the same or different, are independently selected from the group consisting of $C_1$ to $C_6$ alkyl, $C_1$ to $C_6$ alkoxy, $C_1$ to $C_6$ alkylthio, halogen, amino, N-($C_1$ to $C_6$ alkyl)amino, N,N-di($C_1$ to $C_6$ alkyl)amino, phenyl and $C_1$ to $C_6$ alkyl substituted with $C_1$ to $C_6$ alkoxy;
$R^1$ is selected from the group consisting of hydrogen, benzoyl and the alkali metals;
$R^2$ is selected from the group consisting of $C_1$ to $C_6$ alkyl, $C_1$ to $C_6$ haloalkyl, $C_2$ to $C_6$ alkenyl and $C_2$ to $C_6$ alkynyl;
$R^3$ is selected from the group consisting of $C_1$ to $C_6$ alkyl;
$R^4$ is hydrogen; and
n is zero or an integer selected from 1 and 2.

Even more preferred compounds of the invention include those compounds of formulae:

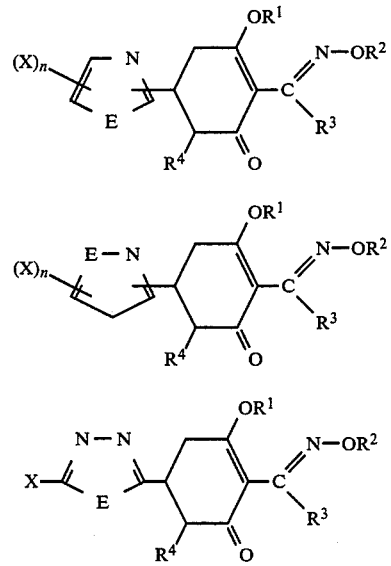

wherein:
E is selected from oxygen and sulfur;

X, which may be the same or different, are independently selected from the group consisting of halogen, $C_1$ to $C_3$ alkyl, $C_1$ to $C_3$ alkoxy and $C_1$ to $C_3$ alkylthio;

$R^1$ is selected from the group consisting of hydrogen and the alkali metals;

$R^2$ is selected from the group consisting of $C_1$ to $C_3$ alkyl, $C_1$ to $C_3$ fluoroalkyl, allyl and propargyl;

$R^3$ is selected from the group consisting of $C_1$ to $C_3$ alkyl;

$R^4$ is hydrogen; and n is zero or an integer selected from 1 and 2.

Particularly preferred values for X include methyl methoxy, methylthio and chlorine;

Particularly preferred values for $R^1$ include hydrogen and the alkali metals.

Particularly preferred values for $R^2$ include ethyl, fluoroethyl, allyl and propargyl.

Particularly preferred values for $R^3$ include ethyl and n-propyl.

Particularly preferred $R^4$ is hydrogen.

Particularly preferred n is zero or an integer selected from 1 and 2.

Specific examples of the compounds of the invention include those compounds detailed in Tables 1a, 1b and 1c below.

TABLE 1a

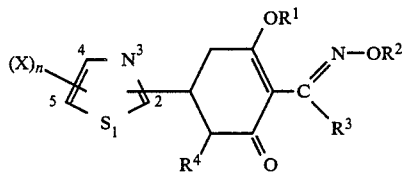

| Compound No | $(X)_n$ | Link | $R^1$ | $R^2$ | $R^3$ | $R^4$ |
|---|---|---|---|---|---|---|
| 1 | all H | 2 | H | $C_2H_5$ | n-$C_3H_7$ | H |
| 2 | 4,5-$(CH_3)_2$ | 2 | H | $C_2H_5$ | n-$C_3H_7$ | H |
| 3 | 2-$CH_3$ | 5 | H | $C_2H_5$ | n-$C_3H_7$ | H |
| 4 | 2-$C_6H_5$ | 5 | H | $C_2H_5$ | n-$C_3H_7$ | H |
| 5 | 2,4-$(CH_3)_2$ | 5 | H | $C_2H_5$ | n-$C_3H_7$ | H |
| 6 | 2-$CH_3$ | 4 | H | $C_2H_5$ | n-$C_3H_7$ | H |
| 7 | 2-$CH_3S$ | 5 | H | $C_2H_5$ | $C_2H_5$ | H |
| 8 | 2-$(CH_3)_2$N—4-$CH_3$ | 5 | H | $C_2H_5$ | n-$C_3H_7$ | H |
| 9 | 4-$CH_3$ | 2 | H | $C_2H_5$ | n-$C_3H_7$ | H |
| 10 | 5-Br—4-$CH_3$ | 2 | H | $C_2H_5$ | $C_2H_5$ | H |
| 11 | a | 2 | H | $C_2H_5$ | n-$C_3H_7$ | H |
| 12 | 2-Cl | 5 | H | $C_2H_5$ | $C_2H_5$ | H |
| 13 | 2-$CH_3O$ | 5 | H | $C_2H_5$ | $C_2H_5$ | H |
| 14 | 5-$CH_3$ | 2 | H | $C_2H_5$ | $C_2H_5$ | H |
| 15 | 4,5-$(CH_3)_2$ | 2 | H | $C_2H_5$ | $C_2H_5$ | H |
| 16 | 2-Cl | 5 | H | | $C_2H_5$ | $C_2H_5$ | b |
| 17 | 2-$CH_3$ | 4 | H | $CH_2CH=CH_2$ | n-$C_3H_7$ | H |
| 18 | 2-$CH_3$ | 4 | H | $CH_2CH_2F$ | n-$C_3H_7$ | H |
| 19 | 2-$CH_3$ | 4 | H | $CH_2C\equiv CH$ | n-$C_3H_7$ | H |
| 20 | 4,5-$(CH_3)_2$ | 2 | c | $C_2H_5$ | n-$C_3H_7$ | H |
| 21 | 2-$CH_3$ | 4 | Na | $C_2H_5$ | n-$C_3H_7$ | H |

Code:
a - 5-($CH_3OCH_2CH_2$)—4-$CH_3$
b - $CO_2CH_3$
c - $COC_6H_5$

TABLE 1b

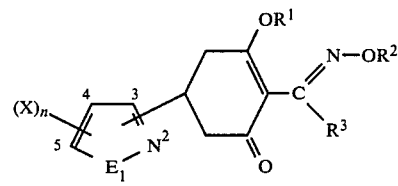

| Compound No | $(X)_n$ | E | Link | $R^1$ | $R^2$ | $R^3$ |
|---|---|---|---|---|---|---|
| 22 | 3,5-$(CH_3)_2$ | O | 4 | H | $C_2H_5$ | $C_2H_5$ |
| 23 | 3-$CH_3$ | S | 5 | H | $C_2H_5$ | $C_2H_5$ |
| 24 | 3-$CH_3$ | S | 5 | H | $CH_2CH=CH_2$ | $C_2H_5$ |

TABLE 1c

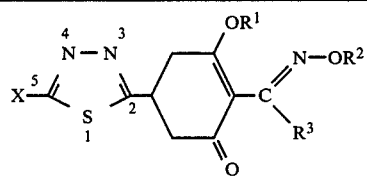

| Compound No | $(X)_n$ | $R^1$ | $R^2$ | $R^3$ |
|---|---|---|---|---|
| 25 | 5-$CH_3S$ | H | $C_2H_5$ | $C_2H_5$ |
| 26 | 5-$CH_3$ | H | $C_2H_5$ | $C_2H_5$ |

The compounds of the invention may be prepared by by a variety of methods and in a further aspect the invention provides methods for the preparation of compounds of formula I.

Conveniently the preparation of the compounds of the invention can be considered in three or four parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX, or reacting, preferably in the presence of a base, a ketone derivative of formula VIa with an alkanoic acid ester of formula VIIc to give a 5-arylcyclohexan-1,3-dione of formula IX;

(ii) reacting, preferably in the presence of a base, an aldehyde derivative of formula V with a malonic acid ester of formula VIIb to give an arylmethylidenemalonate derivative of formula VIc which is in turn reacted, preferably in the presence of a base, with an acetoacetic acid derivative of formula VIId to give an intermediate of formula VIIIc which may be isolated or hydrolysed directly, preferably in the presence of an acid, to give a 5-arylcyclohexan-1,3-dione of formula IX; or (iii) reacting, preferably in the presence of a base, an aldehyde derivative of formula V with an acetic acid ester of formula IVc to give a 2-arylalkenoate derivative of formula VId which is in turn reacted, preferably in the presence of a base, with an acetoacetic acid ester derivative of formula VIId to give an intermediate of formula VIIIa which may be isolated or hydrolysed directly, preferably in the presence of an acid, to give a 5-arylcyclohexan-1,3-dione of formula IX.

Part B involves the acylation of a compound of formula IX to give a 2-acyl-5-arylcyclohexan-1,3-dione of formula XIII. This reaction may be carried out by reacting a 5-arylcyclohexan-1,3-dione of formula IX with:

(iv) an acid anhydride of formula X in the presence of either an alkali metal salt of the corresponding acid of formula XI or an alkoxide salt of formula XII, wherein M is an alkali metal ion and R is $C_1$ to $C_6$ alkyl;

(v) an acid anhydride of formula X in the presence of the corresponding acid of formula XIV;

(vi) an acid halide of formula XV, wherein hal represents halogen, in the presence of a Lewis acid catalyst;

(vii) a mixture of an acid halide of formula XV and the corresponding acid of formula XIV; or (viii) with an alkali or alkaline earth metal hydride followed by reaction with an acid anhydride of formula X or an acid halide of formula XV.

Alternatively, this acylation reaction may be carried out by:

(ix) reacting a 5-arylcyclohexan-1,3-dione of formula IX with an acid halide of formula XV in the presence of pyridine to give an intermediate O-acyl derivative of formula XVI; and (x) reacting the intermediate of formula XVI with a Lewis acid catalyst;

(xi) reacting the intermediate of formula XVI with the acid of formula XIV; or (xii) reacting the intermediate of formula XVI with imidazole or 4-(N,N-dimethylamino)pyridine.

Part C involves the formation of a compound of the invention of formula I wherein $R^1$ is hydrogen, that is a compound of formula II. This reaction may be carried out either by reacting a 2-acyl-5-arylcyclohexan-1,3-dione of formula XIII with:

(xiii) an alkoxyamine derivative of formula XVII; or (xiv) hydroxylamine to give an intermediate oxime derivative of formula XVIII and reacting that intermediate oxime derivative of formula XVIII with an alkylating agent of formula XIX wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, methanesulfonate and trifluoromethanesulfonate.

Part D involves the formation of a compound of the invention of formula I wherein $R^1$ is a substitutent other than hydrogen.

Compounds of the invention of formula I, wherein $R^1$ forms an ether, acyl and sulfonyl derivative of a compound of formula II, may be prepared from the corresponding compounds of the invention of formula II by reacting with an etherification, acylation or sulfonylation reagent of formula XX.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting 2-acyl-5-(aryl)cyclohexane-1,3-dione derivative of formula XIII with an alkoxyamine derivative of formula XVII to give a compound of the invention of formula II or reacting the 2-acyl-5-(aryl)cyclohexane-1,3-dione derivative of formula XIII with hydroxylamine and alkylating the oxime intermediate of formula XVIII with an alkylating agent of formula XIX, wherein L is a leaving group, to give a compound of the invention of formula II; and optionally reacting the compound of the invention of formula II with a compound of formula XX, wherein L is a leaving group, to give a compound of the invention of formula I.

The structures of the compounds described above are detailed on the following pages wherein φ represents the group

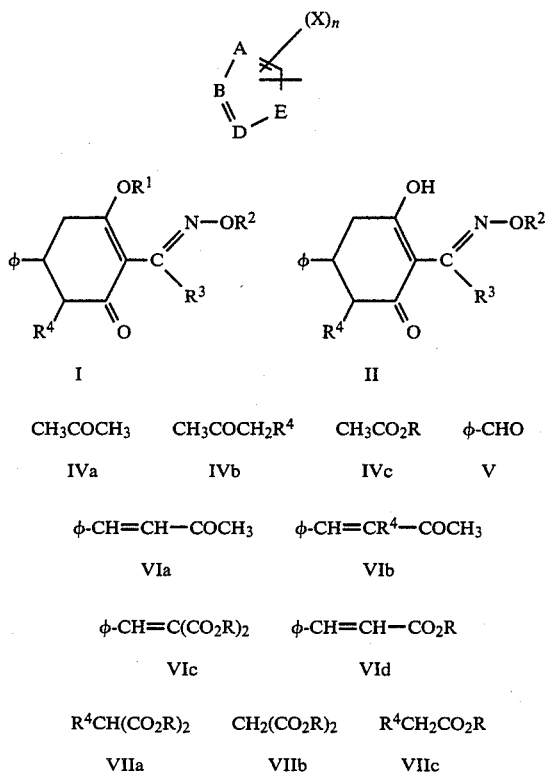

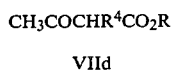 CH₃COCHR⁴CO₂R
VIId

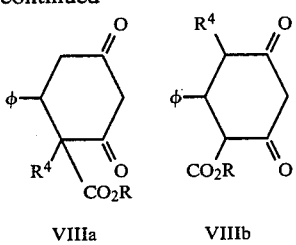
VIIIa  VIIIb

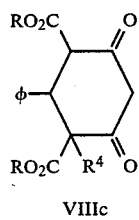
VIIIc

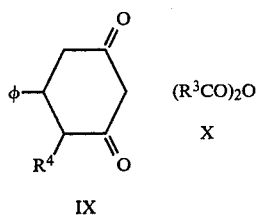
IX (R³CO)₂O
X

R³CO₂M   ROM
XI       XII

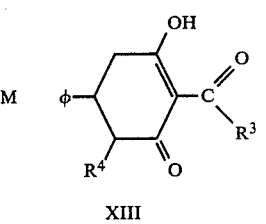
XIII

R³CO₂H   R³COhal
XIV      XV

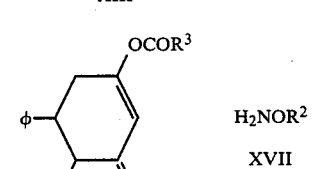
XVI

H₂NOR²
XVII

R²L   R¹L
XIX   XX

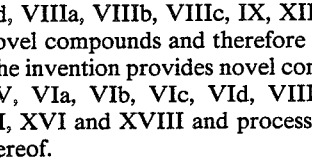
XVIII

Certain of the intermediate compounds of formulae V, VIa, VIb, VIc, VId, VIIIa, VIIIb, VIIIc, IX, XIII, XVI and XVIII are novel compounds and therefore in further embodiments the invention provides novel compounds of formulae V, VIa, VIb, VIc, VId, VIIIa, VIIIb, VIIIc, IX, XIII, XVI and XVIII and processes for the preparation thereof.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat and other varieties of cereals.

Accordingly, in yet a further aspect the invention provides a process for controlling monocotyledonous weeds in cultivated crops, especially wild grasses in cereal crops such as wheat, which process comprises applying to the crop, or to the growth medium of the crop a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an agriculturally acceptable carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown by compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an agriculturally acceptable carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the performed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium sats of arylsulfonic acids including the salts of naphthalenesulfonic acids such as butylnaphthalenesulfonic acids, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water, mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compostions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 5 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3,-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;
E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diruon) and N,N-dimethyl-N'-[3-(trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);
H. 2-phenylpyridazin-3-ones such as 5-amino-4-chloro-2-phenylpyridazin-3-one (common name pyrazon);
I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);
J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(iso-propylamino)-6-methylthio-1,3,5-triazine (common name aziproptryne);
K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);
L. thiolcarbamate herbicides such as S-propyl dipropyl-thiocarbamate (common name verolate);
M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);
N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);
O. anilide herbicides such as N-butoxymethyl-α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);
P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);
Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)glycine (common name glyphosphate) and its salts and esters.

The invention is now illustrated by but in no way limited to the following Examples.

EXAMPLE 1

This example details the preparation of the heterocyclic aldehydes of formula V which were used in the preparation of the compounds of the invention of formula I.

Method A: The aldehydes were prepared by the condensation of bromomalonidialdehyde with the appropriate thiocarbide following the general method described in German Pat. No. 1 182 234 (Chem. Abstracts 62: 7764d). The products were characterized by proton magnetic resonance spectroscopy and the details are recorded in Table 2 below.

Method B: The aldehydes were prepared from the corresponding bromo substituted heterocycle using n-butyllithium and N-formylpiperidine following the general method described by Buttimore et al (J. Chem. Soc., 2032, 1963). The products were characterized by proton magnetic resonance spectroscopy and the details are recorded in Table 2 below.

Method C: The aldehydes were prepared from the corresponding parent heterocycle by lithiation with n-butyl lithium, followed by formylation with N-formylpiperidine following the general method described by P Iversen et al (Acta Chem. Scand., 20, 2649 (1966)). The products were characterized by proton magnetic resonance spectroscopy and the details are recorded in Table 2 below.

Method D: The aldehydes were prepared from the appropriate methyl substituted heterocycle following the method of F Kröhnke (Angew. Chem. Internat. Edit., 2, 380 (1963)). The products were characterized by proton nuclear magnetic resonance spectroscopy and the details are recorded in Table 2 below.

TABLE 2

Aldehyde Precursors to the Compounds of Formula I

| $(X)_n$ | E | Link | Method and/or Literature Reference | Proton Chemical Shift $\delta$ in ppm ($CDCl_3$) |
|---|---|---|---|---|

(structure: $(X)_n$ on 4,5 positions of ring with $N^3$ at 3, $S_1$ at 1, CHO at 2)

| $(X)_n$ | E | Link | Method/Ref | Shift |
|---|---|---|---|---|
| all H | | 2 | B | Not recorded. |
| 4,5-$(CH_3)_2$ | | 2 | B | 2.44(3H,s); 2.48(3H,s); 9.83(1H,s) |
| 2-$CH_3$ | | 5 | A (Chem Abs. 62; 7764d) | 2.78(3H,s); 8.22(1H,s); 9.91(1H,s). |
| 2-$C_6H_5$ | | 5 | A (Chem Abs. 62; 7764d) | 7.35–7.50(3H,m); 7.85–8.05(2H,m); 8.34(1H, s); 9.96(1H,s). |
| 2,4-$(CH_3)_2$ | | 5 | B | 2.70(3H,s); 2.74(3H,s); 10.02(1H,s). |
| 2-$CH_3$ | | 4 | Chem. Ber., 101, 3872 (1968) | 2.78(3H,s); 8.08(1H,s); 9.97(1H,s). |
| 2-$CH_3S$ | | 5 | A | 2.67(3H,s); 8.14(1H,s); 9.85(1H,s). |
| 2-$(CH_3)_2N$— 4-$CH_3$ | | 5 | J. Chem. Soc Perkin Trans I, 341 1983 | 2.52(3H,s); 3.20(6H,s); 9.72(1H,s). |
| 4-$CH_3$ | | 2 | C | 2.58(3H,s); 7.39(1H,s); 10.00(1H,s). |
| 5-Br—4-$CH_3$ | | 2 | D | not recorded |
| 5-($CH_3$—$OCH_2CH_2$)— 4-$CH_3$ | | 2 | C | 2.48(3H,s); 3.07(2H,t); 3.38(3H,s); 3.62(2H,t); 9.86(1H,s). |
| 2-Cl | | 5 | C | 8.20(1H,s); 9.96(1H,s). |
| 2-$CH_3O$ | | 5 | C | 4.19(3H,s); 7.86(1H,s); 9.8(1H,s). |
| 5-$CH_3$ | | 2 | C | 2.57(3H,s); 7.72(1H,s); 9.89(1H,s). |

(structure: $(X)_n$ on 4,5 positions, position 3 with CHO at 3, $N_2$ at 2, $E_1$ at 1)

| $(X)_n$ | E | Link | Method/Ref | Shift |
|---|---|---|---|---|
| 3,5-$(CH_3)_2$ | O | 4 | J. Chem. Soc., Perkin Trans I, 570, 1976 | 2.46(3H,s); 2.69 (3H,s); 9.92 (1H,s). |
| 3-$CH_3$ | S | 5 | B (J. Chem Soc., 2032, 1963) | 2.57(3H,s); 7.53 (1H,s); 10.03(1H,s). |

(structure: X at 5, $S_1$, $N^4$—$N^3$, position 2 with CHO)

| $(X)_n$ | E | Link | Method/Ref | Shift |
|---|---|---|---|---|
| 5-$CH_3S$ | | | D | 2.88(3H,s); 10.09(1H, s). |
| 5-$CH_3$ | | | D (Chem. Abs. 54; 5627b) | 2.8(3H,s); 10.2(1H,s). |

EXAMPLE 2

Preparation of 1-(heterocyclyl)but-1-en-3-ones

The 1-(heterocyclyl)but-1-en-3-ones used in the preparation of the compounds of the invention of formula I were prepared from the appropriate heterocyclic aldehyde by one of the following methods:

(a) An aqueous solution of 2% sodium hydroxide (3 ml) was added to a solution of 2-methyl-thiazole-5-carboxaldehyde (2.5 g) in acetone (20 ml) and water (10 ml). The mixture was stirred for 24 hours at ambient temperature, diluted with water (150 ml) and extracted with chloroform (2×50 ml). The organic layer was washed with water and then dried over anhydrous magnesium sulphate and filtered. Evaporation of the solvent gave 1-(2-methyl-5-thiazolyl)but-1-en-3-one as a low-melting point solid (1.4 g, 43%). Pmr spectrum (CDCl$_3$; δ in ppm); 2.30 (3H, s); 2.72 (3H, s); 6.36 (1H, d); 7.56 (1H, d); 7.74 (1H, s).

(b) A solution of 2,4-dimethylthiazole-5-carboxaldehyde (2.0 g) and 1-triphenylphosphoranylidene-2-propanone (8.2 g) in dimethylsulphoxide (140 ml) was stirred at ambient temperature for 24 hr. The solution was poured into water (400 ml) and extracted with dichloromethane. The dried (Na$_2$SO$_4$) organic extract was evaporated and the residue was purified by column chromatography over silica with ethyl acetate/n-hexane (1:1 v/v) elution to give 1-(2,4-dimethyl-5-thiazolyl)but-1-en-3-one (2.1 g). Pmr spectrum (CDCl$_3$; δ in ppm): 2.32 (3H, s); 2.49 (3H, s); 2.67 (3H, s); 6.30 (1H, d); 7.60 (1H, d).

The specific method used for the preparation of each 1-(heterocyclyl)but-1-en-3-one is indicated in Example 4, Table 5.

EXAMPLE 3

Preparation of 2-acyl-3-hydroxy-5-(heterocyclyl)cyclohex-2-en-1-ones

The 2-acyl-3-hydroxy-5-(heterocyclyl)cyclohex-2-en-1-ones used in the preparation of the compounds of the invention of formula I were prepared from the appropriate 1-(heterocyclyl)but-1-en-3-one either by Method (a) below, or by Method (b) below which involves isolation of the intermediate 3-hydroxy-5-(heterocyclyl)cyclohex-2-en-1-one.

(a) Diethyl malonate (1.5 g) was added to a solution of sodium (0.22 g) in dry absolute ethanol (20 ml) and the mixture was warmed to 60° C. with stirring. 1-(2-Methyl-5-thiazolyl)-but-1-en-3-one (1.4 g) was added and the mixture was boiled under reflux for 2 hours. The ethanol was then completely removed under reduced pressure and dry dimethylformamide (20 ml) was added to the residue. The mixture was heated with stirring under nitrogen to 110° C. and n-butyric anhydride (1.5 ml) was added. After 30 min, the solvent was removed under reduced pressure. An aqueous sodium hydroxide solution (1.5 g in 50 ml) was added to the residue and the mixture was heated under reflux for 5 hours. The hot solution was acidified (to pH 4.5) by slow addition of a dilute hydrochloric acid solution. The cooled mixture was extracted with chloroform (2×100 ml). The dried (MgSO$_4$) organic layer was evaporated to give 2-butyryl-3-hydroxy-5-(2-methyl-5-thiazolyl)cyclohex-2-en-1-one (0.7 g; 30%) as low melting-point solid. Pmr spectrum (CDCl$_3$; δ in ppm): 1.0 (3H, t); 1.7 (2H, m); 2.68 (3H, s); 2.5–3.8 (7H, m); 7.38 (1H, s); OH not observed.

(b) (i) Diethyl malonate (1.16 g) was added to a solution of sodium (158 mg) in dry absolute ethanol (10 ml) and the mixture was heated to reflux. 1-(2-Thiazolyl)-but-1-en-3-one (1.0 g) in dry absolute ethanol (5 ml) was added dropwise to the solution. After refluxing for 2.5 hr, an aqueous potassium hydroxide solution (862 mg in 12 ml) was added and the mixture was extracted with diethyl ether. The aqueous layer was heated to 70° C. and neutralised with dilute hydrochloric acid and the water was then evaporated under reduced pressure. The residue was extracted with dry dimethylformamide. Evaporation of the solvent gave 3-hydroxy-5-(2-thiazolyl)cyclohex-2-en-1-one.

(ii) sodium hydride (135 mg) was added to a solution of 3-hydroxy-5-(2-thiazolyl)cyclohex-2-en-1-one (1.0 g) in dry dimethylformamide (20 ml). The mixture was heated to 60° C. under nitrogen. n-Butyric anhydride (886 mg) was added and the mixture was stirred and heated at 120° C. for 2.5 hr. After cooling, the mixture was poured into a dilute hydrochloric acid solution which was then extracted with dichloromethane. The organic extract was evaporated and the residue was heated at reflux with an aqueous potassium hydroxide solution (2 g in 50 ml) for 0.5 hr. After cooling, the solution was washed with dichloromethane (15 ml). The aqueous layer was acidified with dilute hydrochloric acid and the mixture was then extracted with ethyl acetate. The dried (MgSO$_4$) organic extract was evaporated and the residue was purified by column chromatography over silica to give 2-butyryl-3-hydroxy-5-(2-thiazolyl)cyclohex-2-en-1-one as an orange-brown oil. Pmr spectrum (CDCl$_3$; δ in ppm): 0.96 (3H, t); 1.44–1.84 (2H, m); 3.00–3.12 (6H, m); 3.68–4.00 (1H, m); 7.28 (1H, d); 7.72 (1H, d); 18.20 (1H, brs).

All products were characterized by proton nuclear magnetic resonance spectroscopy. Physical data for the 3-hydroxy-5-(heterocyclyl)cyclohex-2-en-1-ones prepared according to method (b) (i) above are recorded in Table 3 below. Physical data and spectroscopic data for the 2-acyl-3-hydroxy-5-(heterocyclyl)cyclohex-2-en-1-ones prepared according to Method (a) and Method (b) (ii) above are recorded in Table 4 below. The specific Method used for the preparation of each 2-acyl-3-hydroxy-5-(heterocyclyl)cyclohex-2-en-1-one is indicated in Example 4, Table 5.

TABLE 3

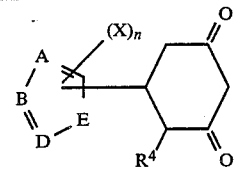

IX

| Intermediate of Formula IX Used in the Preparation of Compound No(s) | Appearance | Proton Chemical Shift (δ in ppm, DMSO-d$_6$) |
|---|---|---|
| 1 | White solid | 2.4–4.0(5H,m); 5.48 (1H,s); 7.2–7.6 (2H,dofd); 10.5(1H, brs). |
| 10 | Brown solid | 2.32(3H,s); 2.3–4.0 (5H,m); 5.50(1H,s); 9.0(1H,brs). |

TABLE 4

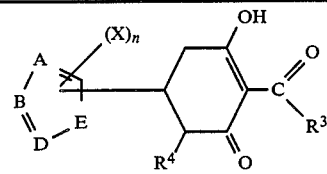

XIII

| Intermediate of Formula XIII Used in the Preparation of Compound No(s) | Appearance | Proton Chemical Shift (δ in ppm, CDCl$_3$) |
|---|---|---|
| 1 | Orange-brown oil | 0.96(3H,t); 1.44– 1.84(2H,m); 3.00–3.12 (6H,m); 3.68–4.00(1H, |

TABLE 4-continued

Structure XIII: cyclohex-2-en-1-one with 3-OH, 2-C(=O)R³, 4-R⁴, 5-[heterocycle with A-B=D-E, (X)ₙ]

| Intermediate of Formula XIII Used in the Preparation of Compound No(s) | Appearance | Proton Chemical Shift (δ in ppm, CDCl₃) |
|---|---|---|
| | | m); 7.28(1H,d); 7.72 (1H,d); 18.20(1H,brs). |
| 2, 20 | Pale brown solid | 0.98(3H,t); 1.4–1.8 (2H,m); 2.29(3H,s); 2.31(3H,s); 2.7–3.9 (7H,m); 18.2(1H,s). |
| 3 | Brown oil | 1.0(3H,t); 1.45–1.85 (2H,m); 2.68(3H,s); 2.5–3.8(7H,m); 7.38 (1H,s). OH not observed. |
| 5 | Brown oil | 0.99(3H,t); 1.64(2H, m); 2.32(3H,s); 2.62 (3H,s); 2.30–3.85(7H, m); 18.25(1H,s). |
| 6, 17, 18, 19, 21 | Pale-brown solid | 0.98(3H,t); 1.45–1.85 (2H,m); 2.69(3H,m); 2.7–3.8(7H,m); 6.80 (1H,s); 18.26(1H,s). |
| 7 | Brown solid | 1.13(3H,t); 2.65(3H, s); 2.7–3.7(7H,m); 7.30(1H,s); 18.18 (1H,s). |
| 8 | Pale yellow solid, mp 130° | 1.00(3H,t); 1.5–1.8 (2H,m); 2.18(3H,s); 2.5–3.0(6H,m); 3.07 (6H,s); 3.27–3.67(1H, m); 18.31(1H,s). |
| 9 | Pale yellow oil | 0.97(3H,t); 1.45–1.75 (2H,m); 2.2–3.9(7H, m); 2.43(3H,s); 6.80 (1H,s); 18.26(1H,s). |
| 10 | Brown oil | 1.13(3H,t); 2.35 (3H,s); 2.3–3.8(7H, m); 18.21(1H,s). |
| 11 | Orange oil | Not recorded |
| 12 | White solid mp 80° C. | 1.15(3H,t); 2.5–3.79(7H,m); 7.34 (1H,s); 18.25(1H,s). |
| 13 | Yellow solid, mp 91° C. | 1.15(3H,t); 2.6–3.21(6H,m); 3.33–3.67(1H,m); 4.05(3H, s); 6.89(1H,s); 18.31(1H,s). |
| 14 | Pale yellow solid, mp 73° C. | 1.14(3H,t); 2.46(3H, s); 2.75–3.20(6H,m); 3.42–3.84(1H,m); 7.36(1H,s); 18.21 (1H,s). |
| 15 | Pale brown solid | 1.14(3H,t); 2.30 (3H,s); 2.32(3H,s); 2.7–3.7(7H,m); 18.22(1H,s). |
| 22 | Orange oil | 1.16(3H,t); 2.26 (3H,s); 2.37(3H,s); 2.5–3.6(7H,m); 18.17(1H,s). |
| 23, 24 | Pale yellow oil | 1.10(3H,t); 2.47 (3H,s); 2.34–3.34 (6H,m); 3.47–4.14 (1H,m); 6.81(1H,s); 18.2(1H,brs). |
| 25 | Orange oil | 1.14(3H,t); 2.77(3H, s); 2.7–4.0(7H,m); 18.23(1H,s). |
| 26 | Brown oil | 1.14(3H,t); 2.75 (3H,s); 2.7–4.0(7H, m); 18.2(1H,brs). |

EXAMPLE 4

Preparation of the compounds of the invention of formula I

The compounds of the invention of formula I indicated in Table I were prepared from the appropriate 2-acyl-3-hydroxy-5-(heterocyclyl)cyclohex-2-en-1-one by one of methods (a) to (d) below.

(a)

2-[1-(Ethoxyimino)butyl]-3-hydroxy-5-(2-methyl-5-thiazolyl)cyclohex-2-en-1-one (3)

Ethoxyamine hydrochloride (0.3 g) and then aqueous sodium hydroxide (0.12 g in 1 ml of water) were added to a solution of 2-butyryl-3-hydroxy-5-(2-methyl-5-thiazolyl)cyclohex-2-en-1-one (0.7 g) in ethanol (50 ml) at 20° C. with stirring. After 20 hours, the mixture was diluted with water (200 ml) and then extracted with chloroform (2×100 ml). The dried (MgSO₄) organic extract was evaporated to give 2-[1-ethoxyimino)butyl]-3-hydroxy-5-(2-methyl-5-thiazolyl)cyclohex-2-en-1-one (0.75 g, 95%) as a nearly colourless oil which was characterised by proton magnetic resonance spectroscopy (CDCl₃; δ in ppm); 0.96 (3H, t); 1.31 (3H, t); 1.7 (2H, m); 2.65 (3H, s); 2.5–3.8 (7H, m); 4.10 (2H, q); 7.37 (1H, s); 15.1 (1H, brs).

(b)

2-[1-(Ethoxyimino)propyl]-3-hydroxy-5-(3-methyl-5-isothiazolyl)cyclohex-2-en-1-one (23)

Ethoxyamine hydrochloride (0.638 g, 6.38 mmol) and then sodium acetate (0.523 g, 6.38 mmol) were added to a solution of 2-propionyl-3-hydroxy-5-[5-(3-methylisothiazolyl]cyclohex-2-en-1-one (1.69 g, 6.38 mmol) in ethanol (40 ml). The mixture was was stirred at room temperature overnight and then the ethanol was removed by evaporation under reduced pressure. The residue was partitioned between water and dichloromethane. The organic layer was separated, dried (Na₂SO₄) and evaporated to yield 2-[1-(ethoxyimino)propyl]-3-hydroxy-5-(3-methyl-5-isothiazolyl)cyclohex-2-en-1-one (950 mg, 48%) as a light brown oil.

(c)

2-[1-(Ethoxyimino)butyl]-3-benzoyloxy-5-(4,5-dimethyl-2-thiazolyl)cyclohex-2-en-1-one (20)

Benzoyl chloride (0.12 g) and 4-methylpyridine (0.08 g) were added dropwise with stirring to a solution of 2-[1-(ethoxyimino)butyl]-5-(4,5-dimethyl-2-thiazolyl)-3-hydroxycyclohex-2-en-1-one (2) (0.27 g) in dichloromethane (40 ml) at ambient temperature. After 1 hour the solution was washed with cold dilute aqueous sodium hydroxide, followed by cold dilute hydrochloric acid and then dried over magnesium sulphate and evaporated to give 2-[1-(ethoxyimino)butyl]-3-benzoyloxy-5-(4,5-dimethyl-2-thiazolyl)cyclohex-2-en-1-one (0.28 g, 80%) as an orange oil. The product was characterized by proton nuclear magnetic resonance spectroscopy and appropriate physical data are recorded in Example 5 Table 6.

(d) Sodium salt of 2-[1-(ethoxyimino)butyl]-3-hydroxy-5-(2-methyl-4-thiazolyl)cyclohex-2-en-1-one (21)

2-[1-(Ethoxyimino)butyl-3-hydroxy-5-(2-methyl-4-thiazolyl)cyclohex-2-en-1-one (6) (0.36 g) and sodium hydroxide (0.05 g) were stirred in acetone (20 ml) at room temperature for 1 hour. The solvent was evaporated and the residue was suspended in toluene (20 ml). Evaporation of the toluene gave the sodium salt of 2-[1-(ethoxyimino)butyl]-3-hydroxy-5-(2-methyl-4-thiazolyl)cyclohex-2-en-1-one as a yellow solid (0.30 g).

The specific Method employed for the preparation of each of the 1-(heterocyclyl)but-1-en-3-ones of formula VIa (Example 2) and the 3-hydroxy-5-(heterocyclyl)cyclohex-2-en-1-ones of formula IX (Example 3) and/or 2-acyl-3-hydroxy-5-(heterocyclyl)cyclohex-2-en-1-ones of formula XIII (Example 3) used as intermediates in the preparation of the compounds of the invention of formula I are listed in Table 5 below, together with the specific Method employed for the preparation of the compounds of the invention of formula I.

Each of the compounds of the invention of formula I were characterized by proton nuclear resonance spectroscopy and physical data and spectroscopic data are recorded in Example 5, Table 6.

TABLE 5

| | Method of Preparation of Compounds of Formulae | | |
|---|---|---|---|
| Compound No | VIa Example 2 Method | IX and XIII Example 3 Method | I Example 4 Method |
| 1 | a | b | a |
| 2 | a | a | a |
| 3 | a | a | a |
| 4 | a | a | a |
| 5 | b | a | a |
| 6 | b | a | a |
| 7 | b | a | a |
| 8 | a | a | b |
| 9 | b | a | b |
| 10 | b | b | b |
| 11 | b | a | b |
| 12 | b | a | b |
| 13 | b | a | b |
| 14 | b | a | b |
| 15 | b | a | a |
| 16 | b | a | b |
| 17 | b | a | b |
| 18 | b | a | b |
| 19 | b | a | b |
| 20 | a | a | c |
| 21 | b | a | d |
| 22 | b | a | b |
| 23 | b | a | b |
| 24 | b | a | b |
| 25 | b | a | b |
| 26 | b | a | b |

EXAMPLE 5

The compounds of the invention of formula 1 were characterized by and may be identified by their proton nuclear resonance spectra. For convenience physical data and pmr spectroscopic data for the compounds of formula I are recorded in Table 6 below.

TABLE 6

| Compound No | Appearance | Proton Chemical Shift δ in ppm (CDCl$_3$) |
|---|---|---|
| 1 | Orange-brown oil | 0.96(3H,t); 1.32(3H,t); 1.55 (2H,m); 2.86–3.9(7H,m); 4.11 (2H,q); 7.27(1H,d); 7.73(1H, d); 14.00(1H,brs). |
| 2 | Light brown solid, mp 85° C. | 0.95(3H,t); 1.31(3H,t); 1.53 (2H,m); 2.29(6H,s); 2.3–3.9 (7H,m); 4.10(2H,q); 14.98(1H, s). |
| 3 | Colourless oil | 0.96(3H,t); 1.31(3H,t); 1.7 (2H,m); 2.65(3H,s); 2.5–3.8 (7H,m); 4.10(2H,q); 7.37(1H, s); 15.1(1H,brs). |
| 4 | Pale yellow oil | 0.98(3H,t); 1.32(3H,t); 1.58 (2H,m); 2.7–3.8(7H,m); 4.12 (2H,q); 7.4–7.9(6H,m); 15.22 (1H,s). |
| 5 | Light brown oil | 0.99(3H,t); 1.33(3H,t); 1.59 (2H,m); 2.32(3H,s); 2.62(3H, s); 2.3–3.9(7H,m); 4.13(2H, q); OH not observed. |
| 6 | Light brown solid, mp 68–70° C. | 0.96(3H,t); 1.31(3H,t); 1.5 (2H,m); 2.69(2H,s); 2.7–4.0 (7H,m); 4.10(2H,q); 6.79(1H, s); 15.0(1H,brs). |
| 7 | Pale brown solid | 1.15(3H,t); 1.33(3H,t); 2.66 (3H,s); 2.6–3.1(6H,m); 3.4– 3.8(1H,m); 4.12(2H,q); 7.39 (1H,s); OH not observed. |
| 8 | Orange oil | 0.99(3H,t); 1.32(3H,t); 1.37–1.71(2H,m); 2.21(3H,s); 2.46–3.00(6H,m); 3.09(6H,s); 3.11–3.60(1H,m); 4.11(2H,q); 15.42(1H,s). |
| 9 | Pale yellow | 0.96(3H,t); 1.32(3H,t); 1.60 (2H,m); 2.2–3.9(7H,m); 2.42 (3H,s); 4.11(2H,q); 6.78(1H, s); OH not observed. |
| 10 | Brown oil | 1.14(3H,t); 1.32(3H,t); 2.36 (3H,s); 2.4–3.1(6H,m); 3.4– 3.8(1H,m); 4.13(2H,q); OH not observed. |
| 11 | Pale yellow | 0.96(3H,t); 1.32(3H,t); 1.55 (2H,m); 2.2–3.9(9H,m); 2.33 (3H,s); 3.37(3H,s); 3.55(2H, t); 4.11(2H,q); OH not observed. |
| 12 | Pale yellow solid, mp 86° C. | 1.07–1.41(6H,m); 2.53–3.10 (6H,m); 3.44–3.73(1H,m); 4.13 (2H,q); 7.34(1H,s); 15.31(1H, brs). |
| 13 | Yellow solid, mp 78° C. | 1.06–1.41(6H,m); 2.55–3.10 (6H,m); 3.33–3.67(1H,m); 4.05 (3H,s); 4.13(2H,q); 6.87(1H, s); 15.08(1H,brs). |
| 14 | Cream solid mp 89° C. | 1.06–1.40(6H,m); 2.45(3H,s); 2.75–3.15(6H,m); 3.43–3.84 (1H,m); 4.12(2H,q); 7.35(1H, s); 15.10(1H,s). |
| 15 | Pale brown solid | 1.14(3H,t); 1.32(3H,t); 2.30 (6H,s); 2.6–3.1(6H,m); 3.4– 3.8(1H,s); 4.13(2H,q); 15.0 (1H,brs). |
| 16 | Yellow oil | 1.06–1.44(6H,m); 2.6–4.2(11H, m); 7.3(1H,s); 15.5(1H,brs). |
| 17 | Yellow oil | 0.97(3H,t); 1.42–1.79(2H,m); 2.51–3.05(6H,m); 2.68(3H,s); 3.36–3.70(1H,m); 4.56(2H,d); 5.24–5.49(2H,m); 5.75–6.21 (1H,m); 6.78(1H,s); 14.08 (1H,s). |
| 18 | Yellow oil | 0.94(3H,t); 1.43–1.75(2H,m); 2.64–3.10(6H,m); 2.69(3H,s); 3.33–3.62(1H,m); 4.07–4.19(1H, m); 4.30–4.50(2H,m); 4.82–4.99 (1H,m); 6.79(1H,s); 14.08(1H, s). |
| 19 | Yellow oil | 0.94(3H,t); 1.43–1.71(2H,m); |

TABLE 6-continued

| Compound No | Appearance | Proton Chemical Shift δ in ppm (CDCl$_3$) |
|---|---|---|
| | | 2.57–3.03(7H,m); 2.69(3H,s); 3.37–3.66(1H,m); 4.63(2H,d); 6.79(1H,s); 13.87(1H,s). |
| 20 | Orange oil | 0.75–1.58(8H,m); 2.33(6H,s); 2.36–3.34(6H,m); 3.72–4.09(3H,m); 7.35–7.66(3H,m); 7.95–8.15(2H,m). |
| 21 | Pale yellow solid | (DMSOd$_6$) 0.74(3H,t); 1.03–1.49 (5H,m); 2.06–2.69(6H,m); 2.60 (3H,s); 3.03–3.49(1H,m); 3.89 (2H,q); 7.04(1H,s). |
| 22 | Yellow oil | 1.17(3H,t); 1.34(3H,t); 2.28 (3H,s); 2.38(3H,s); 2.5–3.5(7H, m); 4.14(2H,q); 15.0(1H,brs). |
| 23 | Light brown oil | 1.15(3H,t); 1.33(3H,t); 2.46 (3H,s); 2.54–3.60(6H,m); 3.66 (1H,m); 4.12(2H,q); 6.8(1H,s); 15.2(1H,brs). |
| 24 | Brown oil | 1.15(3H,t); 2.44(3H,s); 2.61–3.04(6H,m); 3.56–3.85(1H,m); 4.56(2H,d); 5.17–5.51(2H,m); 5.77–6.20(1H,m); 6.83(1H,s); 15.44(1H,s). |
| 25 | Pale brown solid | 1.16(3H,t); 1.33(3H,t); 2.78 (3H,s); 2.8–3.2(6H,m); 3.7–4.0 (1H,m); 4.13(2H,q); OH not observed. |
| 26 | Brown oil | 1.15(3H,t); 1.33(3H,t); 2.76 (3H,s); 2.8–3.1(6H,m); 3.7–4.0. (1H,m); 4.12(2H,q); 15.0(1H, brs). |

EXAMPLE 6

This non-limiting Example illustrates the preparation of formulations of the compounds of the invention.

(a) Emulsifiable Concentrate

Compound No 7 was dissoloved in toluene containing 7% V/V "Teric" N13 and 3% v/v "Kemmat" SC15B to given an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 7 (5 parts by weight) and "Dyapol" PT (1 part by weight) were added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol).

(c) Emulsifiable Concentrate

Compound No 7 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 7 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Stength Concentrate

Compound No 7 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 7 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 7 and 8, in the evaluation of the pre-emergence and post-emergence herbicidal activity of the compounds.

EXAMPLE 7

The pre-emergent herbicidal activity of the compounds of the invention formulated as described in Example 6 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glass house and the effect of the treatment was visually assessed. The results are presented in Table 7 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |

| | | |
|---|---|---|
| Ms | Mustard | |
| Sf | Sunflower | |

TABLE 7

Pre-emergence Herbicidal Activity

| Compound No | APPLICATION Rate (kg/ha) | TEST PLANT | | | | | | | |
|---|---|---|---|---|---|---|---|---|---|
| | | Wh | Ot | Rg | Jm | P | Ip | Ms | Sf |
| 3 | 0.5 | 0 | 0 | 2 | 1 | 0 | 0 | 0 | 0 |
| 5 | 1.0 | 0 | 3 | 4 | 5 | 0 | 0 | 0 | 0 |
| 5 | 0.25 | 0 | 0 | 3 | 3 | 0 | 0 | 0 | 0 |
| 6 | 1.0 | 5 | 4 | 5 | 5 | 0 | 0 | 0 | 0 |
| 6 | 0.25 | 0 | 2 | 5 | 5 | 0 | 0 | 0 | 0 |
| 7 | 1.0 | 3 | 4 | 5 | 5 | 0 | 0 | 0 | 0 |
| 7 | 0.25 | 1 | 1 | 5 | 4 | 0 | 0 | 0 | 0 |
| 12 | 1.0 | 2 | 5 | 5 | 5 | 0 | 0 | 0 | 0 |
| 12 | 0.25 | 1 | 1 | 4 | 5 | 0 | 0 | 0 | 0 |
| 13 | 1.0 | 3 | 3 | 4 | 5 | 0 | 0 | 0 | 0 |
| 13 | 0.25 | 0 | 2 | 3 | 4 | 0 | 0 | 0 | 0 |
| 17 | 1.0 | 2 | 2 | 5 | 5 | 0 | 0 | 0 | 0 |
| 17 | 0.25 | — | 1 | 2 | 3 | 0 | 0 | 0 | 0 |
| 18 | 1.0 | 2 | 2 | 1 | 5 | 0 | 0 | 0 | 0 |
| 18 | 0.25 | — | 2 | — | — | 0 | 0 | 0 | 0 |
| 19 | 1.0 | 2 | 2 | 5 | 5 | 0 | 0 | 0 | 0 |
| 22 | 1.0 | 5 | 5 | 5 | 5 | 0 | 0 | 0 | 0 |
| 22 | 0.25 | 5 | 5 | 5 | 3 | 0 | 0 | 0 | 0 |
| 23 | 1.0 | 3 | 4 | 5 | 5 | 0 | 0 | 0 | 0 |
| 26 | 1.0 | 5 | 5 | 5 | 5 | 0 | 0 | 0 | 0 |

EXAMPLE 8

The post-emergent herbicidal activity of the compounds of the invention formulated as described in Example 6 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 8 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 8

Post-emergence Herbicidal Activity

| Compound No | APPLICATION Rate (kg/ha) | TEST PLANT | | | | | | | |
|---|---|---|---|---|---|---|---|---|---|
| | | Wh | Ot | Rg | Jm | P | Ip | Ms | Sf |
| 1 | 1.0 | 3 | 4 | 4 | 4 | 0 | 0 | 0 | 0 |
| 1 | 0.25 | 0 | 1 | 4 | 3 | 0 | 0 | 0 | 0 |
| 2 | 1.0 | 0 | 4 | 4 | 5 | 0 | 0 | 0 | 0 |
| 2 | 0.25 | 0 | 4 | 2 | 3 | 0 | 0 | 0 | 0 |
| 3 | 0.5 | 5 | 5 | 5 | 5 | 0 | 0 | 0 | 0 |
| 3 | 0.25 | — | 5 | 5 | 5 | 0 | 0 | 0 | 0 |
| 3 | 0.063 | 3 | 5 | 5 | 5 | 0 | 0 | 0 | 0 |
| 4 | 1.0 | 0 | 4 | 4 | 3 | 0 | 0 | 0 | 0 |
| 5 | 1.0 | 5 | 5 | 5 | 5 | 0 | 0 | 0 | 0 |
| 5 | 0.25 | 4 | 5 | 5 | 5 | 0 | 0 | 0 | 0 |
| 5 | 0.063 | 1 | 4 | 4 | 5 | 0 | 0 | 0 | 0 |
| 6 | 1.0 | 5 | 5 | 5 | 5 | 0 | 0 | 0 | 0 |
| 6 | 0.25 | 1 | 5 | 5 | 5 | 0 | 0 | 0 | 0 |
| 6 | 0.063 | 0 | 3 | 5 | 5 | 0 | 0 | 0 | 0 |
| 7 | 1.0 | 5 | 5 | 5 | 5 | 0 | 0 | 0 | 0 |
| 7 | 0.25 | 5 | 5 | 5 | 5 | 0 | 0 | 0 | 0 |
| 7 | 0.063 | 5 | 5 | 5 | 5 | 0 | 0 | 0 | 0 |
| 9 | 1.0 | 2 | 4 | 5 | 5 | 0 | 0 | 0. | 0 |
| 9 | 0.25 | 0 | 1 | 5 | 5 | 0 | 0 | 0 | 0 |
| 10 | 1.0 | 0 | 5 | 5 | 5 | 0 | 0 | 0 | 0 |
| 10 | 0.25 | 0 | 2 | 3 | 5 | 0 | 0 | 0 | 0 |
| 11 | 1.0 | 1 | 5 | 4 | 5 | 0 | 0 | 0 | 0 |
| 11 | 0.25 | 0 | 2 | 4 | 5 | 0 | 0 | 0 | 0 |
| 12 | 1.0 | 3 | 5 | 5 | 4 | 0 | 0 | 0 | 0 |
| 12 | 0.25 | 2 | 5 | 4 | 3 | 0 | 0 | 0 | 0 |
| 12 | 0.063 | 0 | 4 | 3 | 2 | 0 | 0 | 0 | 0 |
| 13 | 1.0 | 5 | 5 | 5 | 5 | 0 | 0 | 0 | 0 |
| 13 | 0.25 | 5 | 5 | 5 | 5 | 0 | 0 | 0 | 0 |
| 13 | 0.063 | 2 | 5 | 3 | 4 | 0 | 0 | 0 | 0 |
| 14 | 1.0 | 4 | 5 | 5 | 5 | 0 | 0 | 0 | 0 |
| 14 | 0.25 | 3 | 5 | 5 | 5 | 0 | 0 | 0 | 0 |
| 14 | 0.063 | 2 | 4 | 4 | 4 | 0 | 0 | 0 | 0 |
| 15 | 1.0 | 0 | 5 | 5 | 5 | 0 | 0 | 0 | 0 |
| 15 | 0.25 | 0 | 3 | 5 | 5 | 0 | 0 | 0 | 0 |
| 17 | 1.0 | 4 | 5 | 5 | 5 | 0 | 0 | 0 | 0 |
| 17 | 0.25 | 2 | 5 | 5 | 5 | — | — | — | — |
| 17 | 0.063 | — | 1 | 4 | 5 | — | — | — | — |
| 18 | 1.0 | 4 | 5 | 5 | 5 | 0 | 0 | 0 | 0 |
| 18 | 0.25 | 4 | 5 | 5 | 5 | — | — | — | — |
| 18 | 0.063 | — | 5 | 5 | 5 | — | — | — | — |
| 19 | 1.0 | 5 | 5 | 5 | 5 | 0 | 0 | 0 | 0 |
| 19 | 0.25 | 1 | 3 | 4 | 5 | — | — | — | — |
| 19 | 0.063 | — | 1 | 3 | 5 | — | — | — | — |
| 22 | 1.0 | 5 | 5 | 5 | 5 | 0 | 0 | 0 | 0 |
| 22 | 0.25 | 5 | 5 | 5 | 5 | 0 | 0 | 0 | 0 |
| 22 | 0.063 | 5 | 5 | 3 | 5 | 0 | 0 | 0 | 0 |
| 23 | 1.0 | 5 | 5 | 5 | 5 | 0 | 0 | 0 | 0 |
| 23 | 0.25 | 5 | 5 | 5 | 5 | 0 | 0 | 0 | 0 |
| 23 | 0.063 | 0 | 4 | 4 | 5 | 0 | 0 | 0 | 0 |
| 25 | 1.0 | 4 | 4 | 4 | 3 | 0 | 0 | 0 | 0 |
| 25 | 0.25 | 3 | 4 | 3 | 4 | 0 | 0 | 0 | 0 |
| 26 | 1.0 | 5 | 5 | 5 | 5 | 0 | 0 | 0 | 0 |
| 26 | 0.25 | 5 | 5 | 5 | 5 | 0 | 0 | 0 | 0 |
| 26 | 0.063 | 3 | 3 | 5 | 5 | 0 | 0 | 0 | 0 |

EXAMPLE 9

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 9 below. Damage to test plants was assessed after 14 days on a scale of 0 to 5 wherein 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. the results are given in Table 9 below. A dash (-) means no experiment was carried out.

The names of the test plants were as follows:

| | |
|---|---|
| Mz | Maize |
| Ww | Winter wheat |
| Rc | Rice |
| Br | Barley |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |

TABLE 9

| Compound No | APPLICATION Method Rate (kg/ha) | TEST PLANT | | | | | | | | | | |
|---|---|---|---|---|---|---|---|---|---|---|---|---|
| | | Mz | Ww | Rc | Br | Av | Dg | Al | St | Ec | Sh | Ag |
| 1 | PRE 0.2 | 2 | 2 | 4 | — | 4 | 3 | 4 | 2 | 4 | — | 3 |
| 1 | POST 0.2 | 4 | 2 | 3 | — | 4 | 4 | 4 | 4 | 4 | 4 | 2 |
| 2 | POST 0.4 | 4 | 1 | 4 | — | 4 | 2 | 3 | 3 | 4 | 3 | 0 |
| 3 | POST 0.4 | 4 | 4 | 4 | — | 4 | 4 | 4 | 5 | 5 | 4 | 4 |
| 3 | POST 0.2 | 4 | 3 | 4 | — | 4 | 4 | 4 | 4 | 5 | 4 | 4 |
| 3 | POST 0.05 | 4 | 0 | 3 | — | 2 | 3 | 4 | 3 | 4 | 3 | 0 |
| 4 | POST 0.4 | 3 | 0 | 3 | — | 3 | 2 | 4 | 3 | 4 | 3 | 0 |
| 4 | POST 0.2 | 2 | 0 | 1 | — | 3 | 1 | 4 | 3 | 4 | 1 | 0 |
| 5 | POST 0.4 | 4 | 4 | 4 | — | 4 | 4 | 4 | 4 | 5 | 4 | 4 |
| 5 | POST 0.2 | 4 | 3 | 4 | — | 4 | 4 | 4 | 4 | 4 | 4 | 3 |
| 5 | POST 0.05 | 4 | 0 | 1 | — | 0 | 3 | 3 | 3 | 3 | 3 | 0 |
| 6 | POST 0.4 | 3 | 3 | 4 | — | 5 | 4 | 4 | 5 | 5 | 4 | 3 |
| 6 | POST 0.2 | 3 | 2 | 4 | — | 4 | 3 | 4 | 4 | 4 | 2 | 2 |
| 6 | POST 0.05 | 2 | 0 | 4 | — | 4 | 2 | 3 | 4 | 2 | 1 | 1 |
| 7 | POST 0.4 | 4 | 3 | 4 | — | 5 | 4 | — | 4 | 5 | 4 | 3 |
| 7 | POST 0.2 | 4 | 3 | 4 | — | 5 | 4 | — | 3 | 4 | 4 | 1 |
| 7 | POST 0.05 | 2 | 1 | 4 | — | 4 | 3 | — | 3 | 4 | 4 | 1 |
| 8 | POST 0.4 | 4 | 2 | 4 | — | 3 | 4 | 4 | 4 | 4 | 4 | 0 |
| 8 | POST 0.2 | 4 | 1 | 4 | — | 1 | 4 | 3 | 3 | 4 | 4 | 0 |
| 9 | POST 0.4 | 4 | 1 | 4 | — | 4 | 4 | 4 | 4 | 4 | 4 | 2 |
| 9 | POST 0.2 | 4 | 0 | 4 | — | 4 | 4 | 4 | 5 | 4 | — | 1 |
| 9 | POST 0.05 | 1 | 0 | 1 | — | 0 | 3 | 3 | 3 | 3 | 3 | 0 |
| 10 | POST 0.2 | 2 | 0 | 2 | — | 3 | 4 | 4 | 2 | 4 | 4 | 0 |
| 15 | POST 0.2 | 4 | 0 | 4 | — | 4 | 4 | — | 3 | 4 | 4 | 0 |
| 15 | POST 0.1 | 2 | 0 | 2 | — | 4 | 3 | — | 2 | 4 | 2 | 0 |
| 22 | POST 0.2 | 4 | 4 | 4 | — | 4 | 2 | 4 | 4 | 4 | 4 | 4 |
| 22 | POST 0.1 | 4 | 4 | 4 | — | 4 | 3 | 4 | 4 | 4 | 4 | 3 |
| 25 | POST 0.4 | 4 | 4 | 4 | — | 4 | 4 | 4 | 4 | 4 | 4 | 4 |
| 25 | POST 0.2 | 3 | 2 | 2 | — | 4 | 3 | 4 | 4 | 4 | 4 | 3 |
| 25 | POST 0.1 | 2 | 0 | 0 | — | 3 | 3 | 3 | 3 | 2 | 4 | 1 |
| 26 | POST 0.2 | 5 | 4 | 4 | — | 4 | 4 | 4 | 4 | 4 | 4 | 2 |
| 26 | POST 0.05 | 4 | 0 | 1 | — | 2 | 4 | 3 | 4 | 4 | 3 | 0 |

We claim:

1. A compound of formula selected from wherein:
E is selected from oxygen and sulfur;
x, which may be the same or different, are independently selected from the group consisting of halogen, $C_1$ to $C_3$ alkyl, $C_1$ to $C_3$ alkoxy and $C_1$ to $C_3$ alkylthio;
$R^1$ is selected from the group consisting of hydrogen and the alkali metals;
$R^2$ is selected from the group consisting of $C_1$ to $C_3$ alkyl, $C_1$ to $C_3$ fluoroalkyl, allyl and propargyl;
$R^3$ is selected from the group consisting of $C_1$ to $C_3$ alkyl;
$R^4$ is hydrogen; and
n is zero or an integer selected from 1 and 2.

2. A compound according to claim 1 wherein:
E is selected from oxygen and sulfur;
X which may be the same or different, are independently selected from the group consisting of methyl, methoxy, methylthio and chlorine;
$R^1$ is selected from the group consisting of hydrogen, sodium and potassium;
$R^2$ is selected from the group consisting of ethyl, fluoroethyl, allyl and propargyl;
$R^3$ is selected from ethyl and n-propyl;
$R^4$ is hydrogen; and
n is an integer selected from 1 and 2.

3. A compound according to claim 2 selected from the group consisting of:
2-[1-(ethoxyimino)propyl]-3-hydroxy-5-(3,5-dimethylisoxazol-4-yl)cyclohex-2-en-1-one;
2-[1-(allyloxyimino)propyl]-3-hydroxy-5-(3-methylisothiazol-5-yl)cyclohex-2-en-1-one.

4. A herbicidal composition comprising as active ingredient a compound as defined according to claim 1 and a carrier therefor.

5. A process for severely damaging or killing unwanted plants which process comprises applying to said plants, or to the growth medium of said plants, an effective amount of a compound as defined according to claim 1.

6. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

7. A process according to claim 5 or claim 6 wherein the compound is applied at a rate in the range of from 0.005 to 20 kilograms per hectare.

* * * * *